US008976031B2

(12) United States Patent
Ophardt

(10) Patent No.: US 8,976,031 B2
(45) Date of Patent: Mar. 10, 2015

(54) PERSONAL COMPLIANCE DISPENSER

(75) Inventor: Heiner Ophardt, Arisdorf (CH)

(73) Assignee: Gotohti.com Inc., Beamsville (CA)

( * ) Notice: Subject to any disclaimer, the term of this patent is extended or adjusted under 35 U.S.C. 154(b) by 13 days.

(21) Appl. No.: 13/441,711

(22) Filed: Apr. 6, 2012

(65) Prior Publication Data
US 2012/0256741 A1 Oct. 11, 2012

(30) Foreign Application Priority Data

Apr. 8, 2011 (CA) .................................... 2737012

(51) Int. Cl.
| | |
|---|---|
| *G08B 23/00* | (2006.01) |
| *A47K 5/12* | (2006.01) |
| *B05B 11/00* | (2006.01) |
| *G06F 19/00* | (2011.01) |
| *B05B 15/06* | (2006.01) |
| *G08B 21/24* | (2006.01) |

(52) U.S. Cl.
CPC ............. *B05B 11/308* (2013.01); *B05B 15/061* (2013.01); *G06F 19/327* (2013.01); *G08B 21/245* (2013.01)
USPC .............. 340/573.1; 340/539.11; 340/286.07; 340/286.09; 221/91; 221/9; 221/96; 222/23; 222/27; 222/39; 222/52

(58) Field of Classification Search
CPC . G08B 21/245; A47K 5/1207; A47K 5/1217; A61L 2/183; A61L 2/235; A61L 2/0088
USPC ..................................................... 340/573.1
See application file for complete search history.

(56) References Cited

U.S. PATENT DOCUMENTS

| | | | |
|---|---|---|---|
| 4,674,654 A * | 6/1987 | Fujii et al. ........................ 222/39 |
| 6,375,038 B1 * | 4/2002 | Daansen et al. ................. 222/52 |
| 6,542,568 B1 * | 4/2003 | Howes et al. .................... 377/16 |
| 6,698,377 B1 | 3/2004 | Topman et al. |
| 7,708,166 B2 | 5/2010 | Ophardt |
| 7,898,407 B2 * | 3/2011 | Hufton et al. ............. 340/539.11 |
| 8,020,573 B2 * | 9/2011 | Lamers et al. ..................... 137/7 |
| 2004/0069798 A1 * | 4/2004 | Grey et al. ........................ 222/52 |
| 2004/0150527 A1 * | 8/2004 | Harper et al. ............... 340/573.1 |
| 2006/0062408 A1 * | 3/2006 | Cho et al. ......................... 381/177 |
| 2007/0229288 A1 * | 10/2007 | Ogrin et al. ................. 340/573.1 |
| 2008/0020794 A1 * | 1/2008 | Garon et al. ................ 455/556.1 |
| 2008/0246599 A1 | 10/2008 | Hufton et al. |
| 2009/0045221 A1 | 2/2009 | Ophardt et al. |
| 2009/0114679 A1 | 5/2009 | Ophardt et al. |
| 2009/0166381 A1 | 7/2009 | Phelps et al. |
| 2009/0261123 A1 * | 10/2009 | McNiff et al. .................. 222/39 |
| 2010/0073162 A1 | 3/2010 | Johnson et al. |
| 2010/0117836 A1 * | 5/2010 | Seyed Momen et al. .. 340/573.1 |

(Continued)

FOREIGN PATENT DOCUMENTS

| | | |
|---|---|---|
| EP | 2223642 | 9/2010 |
| EP | 2223642 A2 * | 9/2010 |
| GB | 2425388 | 10/2006 |

*Primary Examiner* — Mohammad Ghayour
*Assistant Examiner* — Adnan Aziz
(74) *Attorney, Agent, or Firm* — Thorpe North & Western LLP

(57) ABSTRACT

A portable personal dispenser assembly comprising a combination of a dispenser and a communication enabled, portable handheld pocket-sized, personal computer in which the pocket-sized personal computer performs compliance monitoring of use of the dispenser and preferably controls and powers the use of the dispenser.

13 Claims, 17 Drawing Sheets

(56) References Cited

U.S. PATENT DOCUMENTS

| | | |
|---|---|---|
| 2010/0288788 A1* | 11/2010 | Ophardt .............................. 222/1 |
| 2010/0328076 A1* | 12/2010 | Kyle et al. .................. 340/573.1 |
| 2010/0332022 A1* | 12/2010 | Wegelin et al. ............... 700/231 |
| 2011/0005606 A1 | 1/2011 | Bartels et al. |
| 2011/0011886 A1* | 1/2011 | Zaima et al. ...................... 222/1 |
| 2011/0169643 A1* | 7/2011 | Cartner ...................... 340/573.1 |
| 2011/0169646 A1* | 7/2011 | Raichman .................. 340/573.1 |
| 2012/0212344 A1 | 8/2012 | Forsberg et al. |
| 2013/0033376 A1 | 2/2013 | Seyed Momen |
| 2013/0126554 A1 | 5/2013 | Ophardt et al. |

* cited by examiner

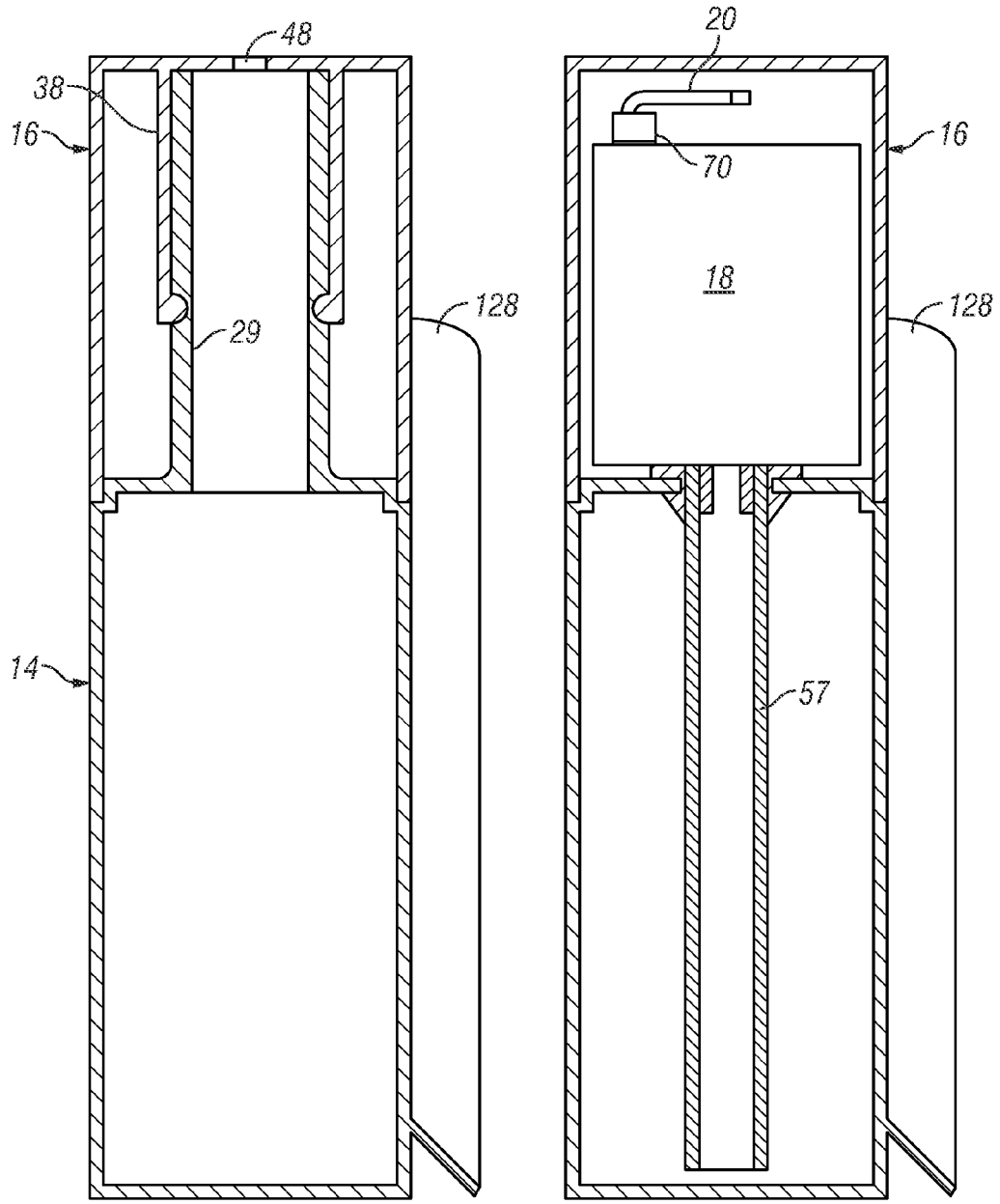

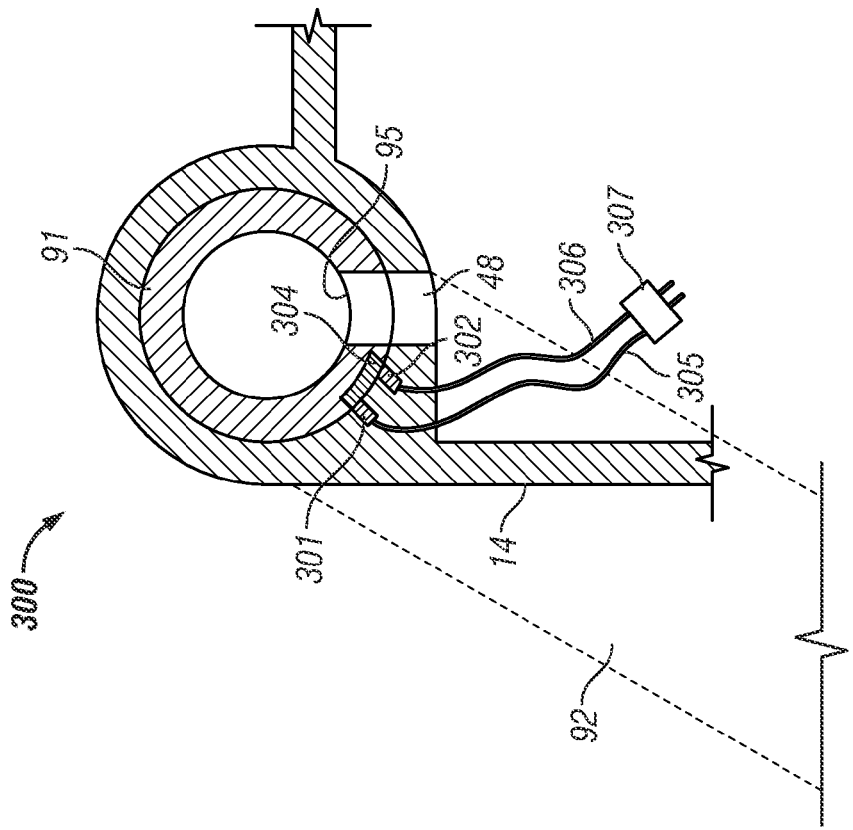
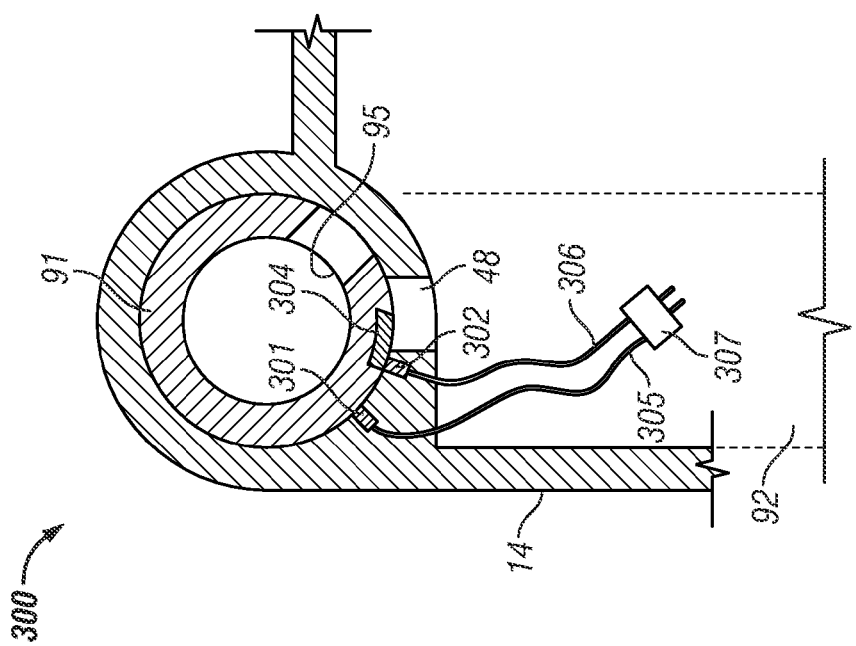

PERSONAL COMPLIANCE DISPENSER

SCOPE OF THE INVENTION

This invention relates to a portable dispenser for disinfecting fluid and, more particularly, to a dispenser assembly in which compliance monitoring of hand hygiene is carried out by a communication enabled, portable handheld pocket-sized, personal computer which preferably is a commercially available smart phone.

BACKGROUND OF THE INVENTION

In hospitals, health care facilities, restaurants and food preparation facilities, proper hand hygiene is important to prevent the spread of infection and disease. Hand hygiene policies which exist for such facilities are preferably enforced by monitoring compliance with the policies. Monitoring compliance permits administrators to monitor and enhance hand hygiene.

Hand hygiene compliance monitoring is known, for example, to monitor the usage of dispensers dispensing disinfecting fluids. Such dispensers may typically be permanently mounted at locations in hospitals as, for example, on the walls and stands. The monitoring is known to monitor the activity of any individual dispenser and may include monitoring of the individual person who uses the dispenser.

Portable body worn fluid dispensers are known for being carried or worn by a person and to dispense hand cleaning disinfectant fluid. However, known such personal fluid dispensers suffer the disadvantage that they do not provide a practical arrangement for compliance monitoring and, as a result, the entire compliance monitoring system is not optimized in that there is no practical compliance monitoring of personal dispensers causing a weakness in compliance monitoring of all dispensers in a facility.

SUMMARY OF THE INVENTION

To at least overcome these disadvantages of previously known devices, the present invention provides a portable personal dispenser assembly comprising a combination of a dispenser and a communication enabled, portable handheld pocket-sized, personal computer in which the pocket-sized personal computer performs compliance monitoring of use of the dispenser and preferably controls and powers the use of the dispenser.

An object of the present invention is to provide an improved portable personal hand disinfecting fluid dispenser to be carried or worn by a user.

In one aspect the present invention provides a personal hand hygiene compliance unit carried on a person for compliance monitoring of hand hygiene, the unit comprising a hand sanitizing fluid dispenser and a communication enabled, not larger than pocket-sized personal computer which is preferably portable and handheld, the dispenser comprising a dispenser housing, a reservoir for containing a fluid, a pump and a discharge outlet, the dispenser housing carrying the reservoir, the pump and the discharge outlet, the pump coupled to the reservoir with the pump in communication with the fluid in the reservoir, the pump capable of being activated to dispense the fluid from the reservoir out the discharge outlet, the pocket-sized personal computer having a computer housing, and within the computer housing a controller, a user interface, a battery and a data communication device for transmission of data from the pocket-sized personal computer, the dispenser housing mechanically coupled to the computer housing, the controller monitoring when the pump is activated and providing for the transmission via the data communication device of data regarding the activation of the pump to a remote computer for compliance monitoring.

The personal compliance device includes a hand sanitizing fluid dispenser. The fluid dispenser includes a fluid reservoir and a pump mechanism to dispense fluid from the reservoir. The pump may comprise an electrically powered pump or a pump which uses manual power to dispense fluid. Preferably, the dispenser is configured to prevent leakage when not in use.

The personal compliance device comprising the combination of the fluid dispenser and the communication enabled, personal computer is to be worn by a user and preferably is pocket-sized, portable and handheld. Therefore, each of the dispenser and the personal computer needs to be of relatively small size and of a shape which facilitates the wearing by a user and a preferred capability to be placed in a wearer's typically sized pocket and more preferably have a length not greater than 5", a width not greater than about 3" and a depth not greater than about 2", such that the personal compliance device preferably fits within a volume of 5" by 3" by 2". The personal compliance device is portable and adapted to be handheld.

The personal compliance device includes a communication enabled, personal computer. The personal computer is to be not larger than pocket-sized, that is, preferably not greater than a size which fits in a typically sized pocket of clothing of a wearer so as to preferably fit within such a pocket of a user, and more preferably, have a length not greater than 5", a width not greater than 3" and a depth not greater than 1" such that the pocket-sized personal computer preferably fits within a volume of 5" by 3" by 1". The pocket-sized personal computer is portable and adapted to be handheld.

The pocket-sized personal computer is communication enabled for at least one of wired connectivity and communication with another computer as by USB and wireless communication as by Wi-Fi (trade mark) communication, Bluetooth (trade mark) communication, and IrDA line of sight wireless communication. The Infrared Data Association (IrDA) defines physical specifications communications protocol standards for the short-range exchange of data over infrared light, for uses such as personal area networks (PANs).

The pocket-sized personal computer is preferably enabled with Wi-Fi (trade mark) communication and/or BLUETOOTH (trade mark) communication. With Wi-Fi enablement connection can be made to other computers such as to a remote host computer and to the Internet when within a range of a wireless network connected to the Internet. Wi-Fi enablement includes various connectivity technologies including wireless local area network (WLAN) and various technologies that support creating personal area network (PAN), local area network (LAN), and wide area network (WAN) connections. BLUETOOTH is a proprietary open wireless technology standard for exchanging data using short wavelength radio transmissions between devices creating personal area networks (PANs).

The pocket-sized personal computer preferably includes data receiving/input capability and at least minimal data storage capability.

The pocket-sized personal computer preferably has at least some capability for output to a wearer preferably with electronic visual display, audio output or vibration and preferably capability for at least some input from a wearer preferably by touch as to keys or a touchpad screen or by audible spoken input commands.

The pocket-sized personal computer is preferably selected from commercially available devices such as smart phones, personal digital assistants (PDA) and pocket personal computer (Pocket PC). A preferred example of suitable commercially available smart phones includes BLACKBERRY (trade mark) smart phones and Apple IPHONE (trade mark) smart phones. One example of one suitable commercially available PDA is the APPLE I-POD (trade mark) with WI-FI enablement. An example of a suitable commercially available PDA and Pocket PC is represented by the products sold by Hewlett Packard under the trade marks HP iPAQ (trade mark).

In accordance with the present invention, the personal compliance device preferably is incorporated as one component in a compliance monitoring system as in a hospital, health care facility or food preparation facility in which all usage of hand sanitizing fluid is desired to be compliance monitored. The communication enabled personal compliance device together with other communication enabled dispensers such as fixedly mounted manually and automatically operated dispensers can serve all the needs for dispensing of hand sanitizing fluid in the facility and together provide compliance monitoring of all dispensing of hand sanitizing fluid in the facility.

BRIEF DESCRIPTION OF THE DRAWINGS

Further aspects and advantages of the present invention will become apparent from the following description taken together with the accompanying drawings in which:

FIG. 7 is a cross-sectional side view along section line 7-7' in FIG. 2;

FIG. 8 is a cross-sectional side view along section 8-8' in FIG. 2;

FIG. 12 is a schematic partial cross-sectional side of the dispenser assembly of FIG. 10 in a closed position;

FIG. 13 is a schematic partial cross-sectional side the same as in FIG. 12 but with the dispenser assembly of FIG. 10 in an open position;

DETAILED DESCRIPTION OF THE DRAWINGS

Figure 1:
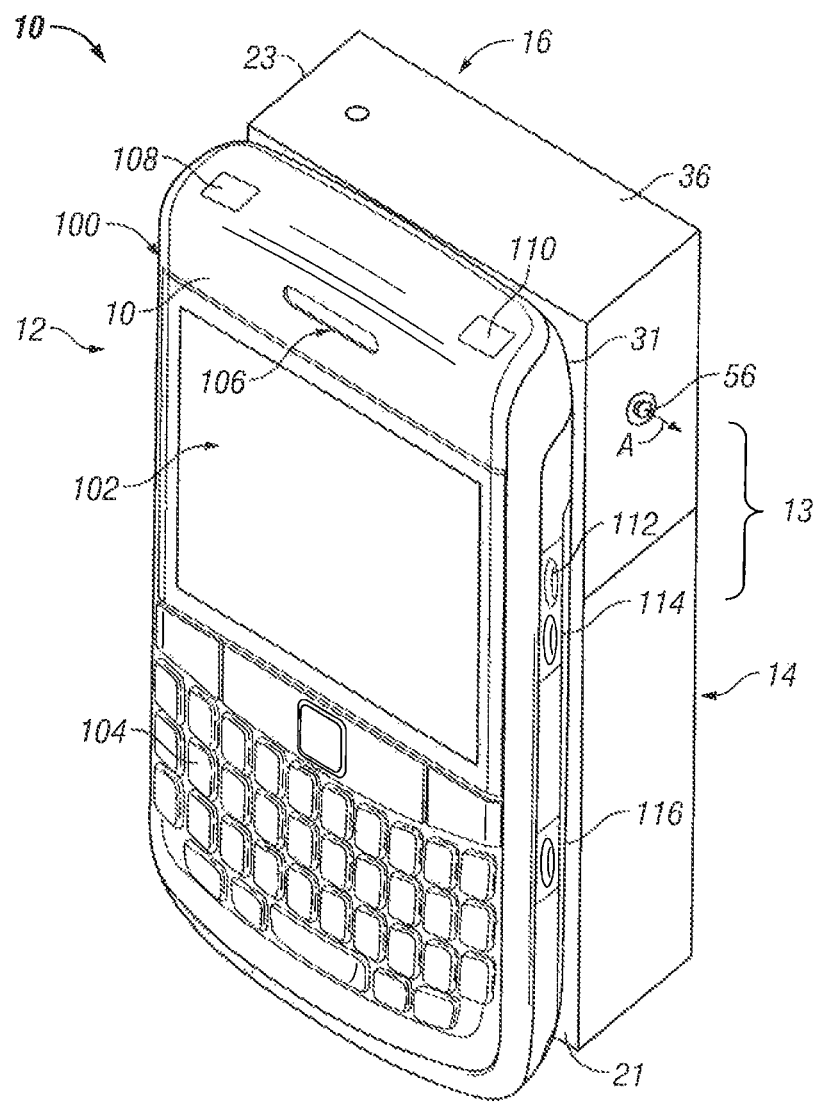
FIG. 1 is a front pictorial view of a personal compliance dispenser assembly in accordance with a first embodiment of the present invention.
Figure 2:
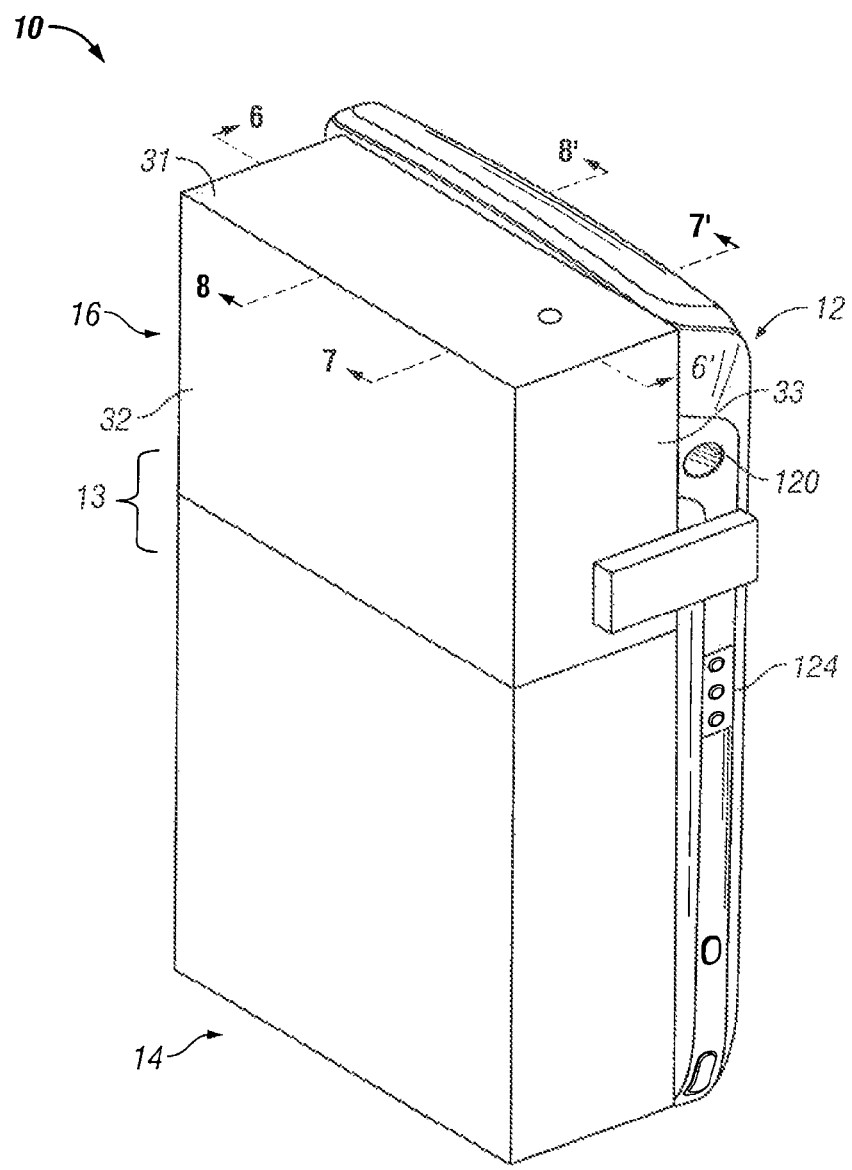
FIG. 2 is a rear pictorial view of the dispenser assembly shown in FIG. 1.
Figures 3, 4:
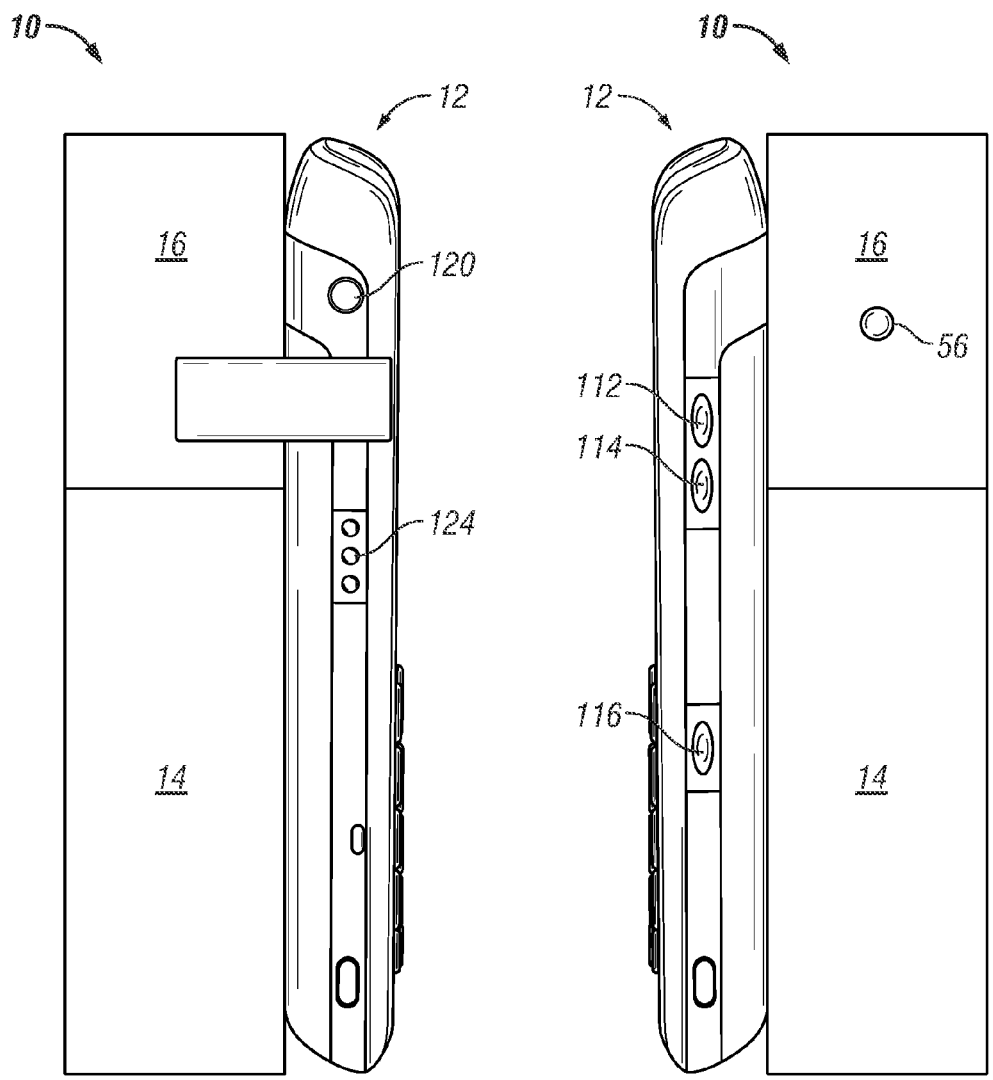
FIG. 3 is a left side view of the dispenser assembly shown in FIG. 1.
FIG. 4 is a right side view of the dispenser assembly shown in FIG. 1.

Reference is made to FIG. 1 as well as FIGS. 2 to 5 showing a personal dispenser assembly 10 in accordance with a first embodiment of the present invention and comprising a communication enabled, portable handheld pocket-sized, personal computer 12 and a dispenser 13. The pocket-sized, personal computer 12 illustrated is a BLACKBERRY 9700 brand smart phone 12 sold under this trade-mark name by Research In Motion Inc. and having, as is known, a main computer housing or casing 100 carrying on its front 101 a display screen 102, a keypad of keys 104, a microphone and speaker 106, carrying on its top a lock key 108 and a mute key 110, carrying on its right side volume keys 112 and 114 and a programmable convenience key 116 typically used to operate a camera 118 seen in FIG. 5 and, carrying on its left side, a headset jack 120, a mini USB port 122 and a convenience key 124 which can be programmed but is typically used to operate voice commands.

The smart phone 12 carries on its rear 126 a battery cover 128 which removably couples with the main casing 100 by sliding upwardly for insertion and downwardly for removal.

Figure 6:
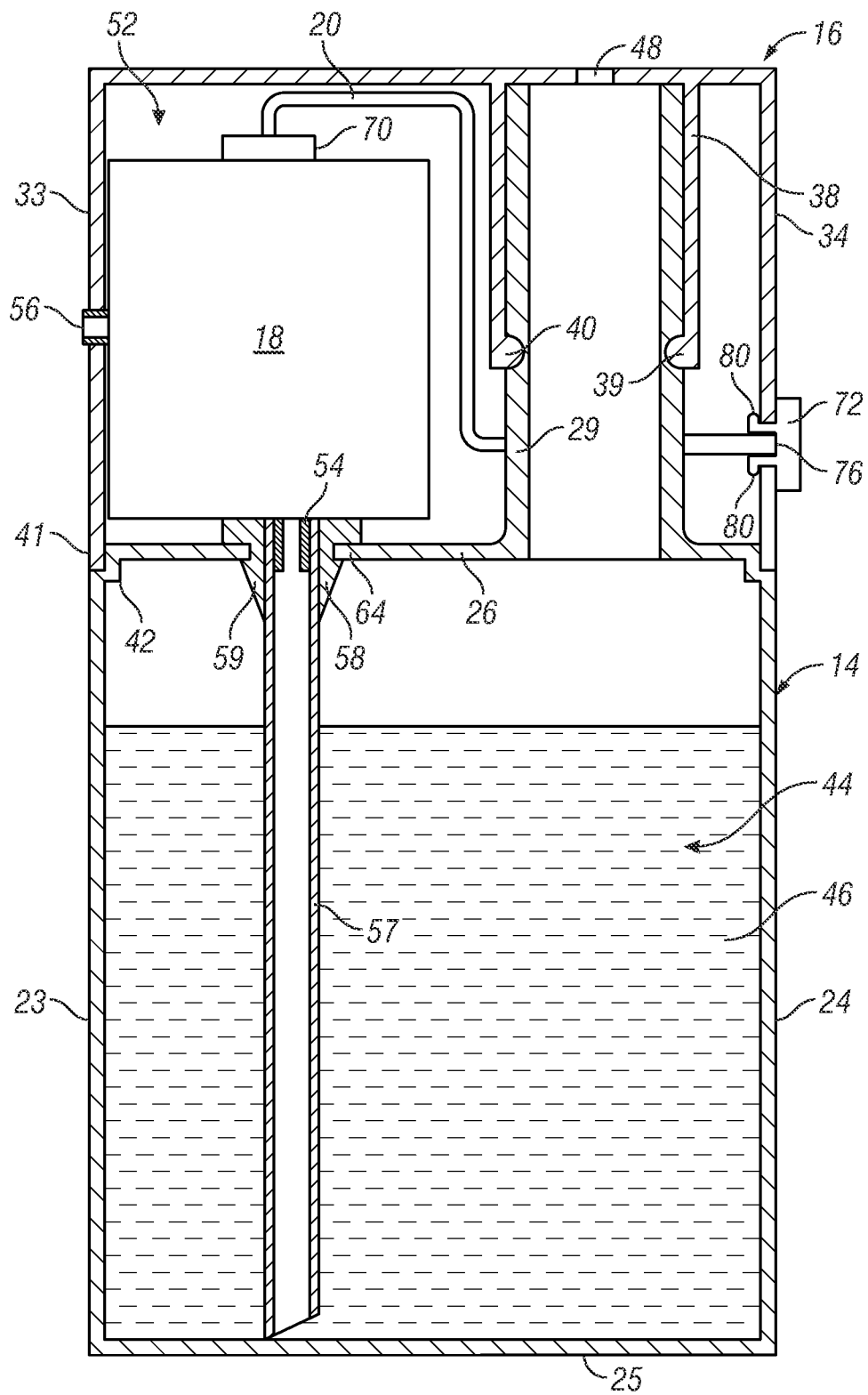
FIG. 6 is a vertical cross-sectional rear view along section line 6-6' in FIG. 2.

As best seen in FIG. 6, the dispenser 13 includes a reservoir 14, a top cover 16, a pump 18 and a patch cord 20.

The reservoir 14 is shown as generally rectangular having a front 21, a back 22, a left side 23, a right side 24, a bottom 25 and a top 26. The reservoir 14 is enclosed but for two openings provided through the top 26 namely a pump opening 27 and a filler opening 28. The filler opening 28 is within an upstanding tube 29 open at an upper end 30. The reservoir 14 defines an enclosed internal space 44 to receive a fluid 46 to be dispensed.

The cover 16 is also generally rectangular in shape having a front 31, a back 32, a left side 33, a right side 34 and a top 36. The cover 16 is open at its bottom such that interior of the cover 16 there is provided a compartment 52.

From an inside surface 37 of the top 36 of the cover 16, a tubular member 38 extends downwardly to a lower end 39. The lower end carries an annular inwardly extending boss 40. The boss 40 is complimentary to an annular groove 41 extending circumferentially about the tube 29 on the reservoir. The tubular member 38 is sized to be coaxially slidably disposed snug about the tube 29 of the reservoir 14 with the boss 40 engaged in snap fit in the groove 41 forming a fluid impermeable seal therewith and to snap fit the cover 16 onto the reservoir 14 to resist upward removal. As seen in FIG. 6, the reservoir 14 carries a ledge 42 which extends circumferentially about the top 26. A lower edge 41 of each of the front 31, back 32 and two sides 33 and 34 of the cover 16 are received in the annular ledge 42 about the reservoir 14 so as to prevent relative rotation of the cover 16 relative to the reservoir 14 about the tube 29.

As seen in FIGS. 6 and 7, the top 36 of the cover 16 has an air vent opening 48 therethrough open into the tube 29 to provide an entrance for air into the reservoir space 44 such that when fluid 46 is dispensed from the reservoir by the pump 18, air may enter the reservoir to avoid buildup of a vacuum within the reservoir space 44. A vent plug 50, not shown, may be provided for manual movement between opened and closed position to sealably close the air vent opening 48.

Figure 9:
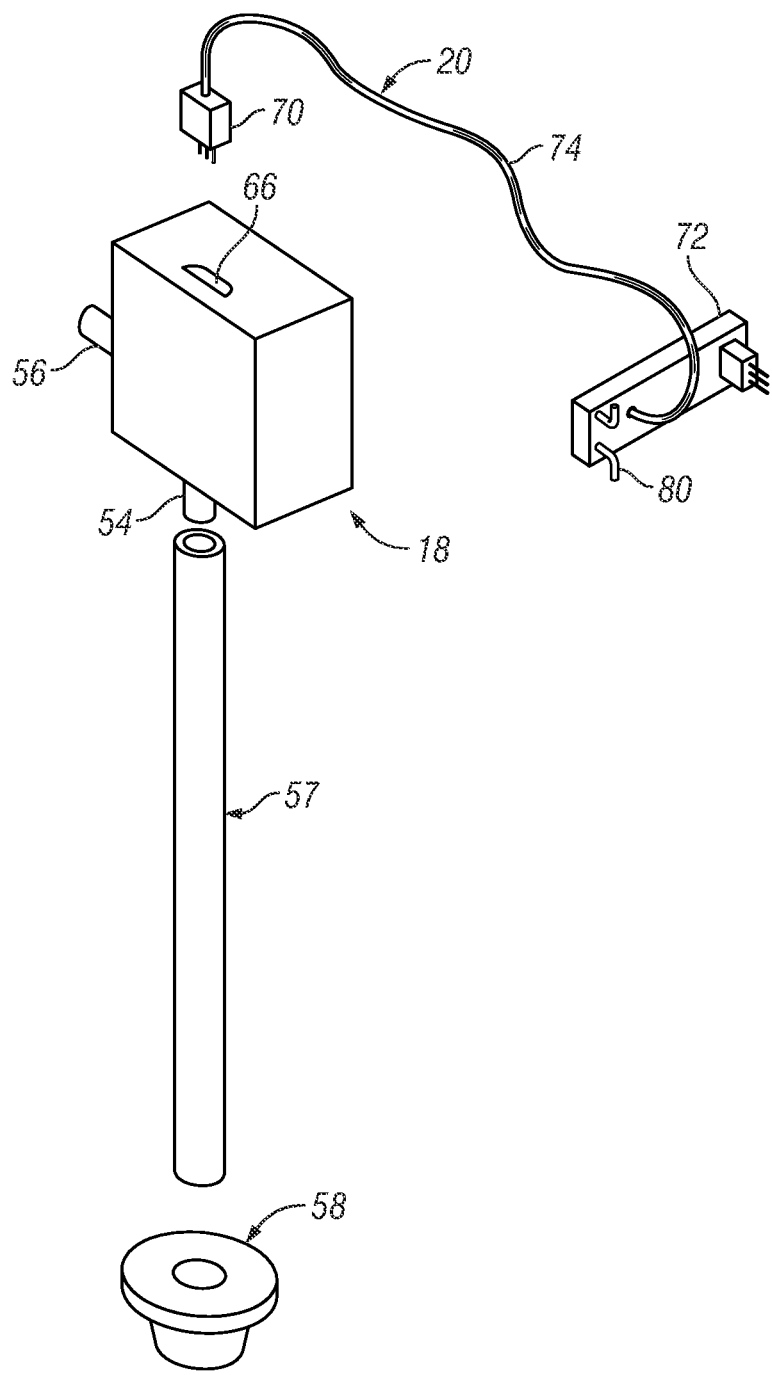
FIG. 9 is a schematic exploded pictorial view of the pump and patch cord.

The pump 18 is removably located within the compartment 52 within the cover 16. The pump 18 is preferably is a piezoelectric diaphragm micro pump having an inlet tube 54 and an outlet tube 56 as seen in FIGS. 6, 8 and 9. The inlet tube 54 has a dip tube 57 sealably engaged coaxially thereabout. A resilient stopper member 58 coaxially overlies the dip tube 57. The resilient stopper 58 carries an annular slotway 59 thereabout sized to receive the circumferential edge 64 of the pump opening 27 therein so as to removably sealably couple the pump 18 to the reservoir 14 in a sealed friction fit relation. The dip tube 57 extends downwardly inside the reservoir 14 to proximate the bottom 25 of the reservoir 14.

The pump 18 has a female mini USB port 66.

The patch cord 20 comprises an elongate flexible wire 74 comprising a grouping of insulated electrical conductors. The patch cord 20 has at one first end a male pump connector 70 to be received in the female mini USB port 66 of the pump 18 and at the other second end a male phone connector 72 to be removably received within the mini USB port 122 on the smart phone 12.

The wire 74 of the patch cord 20 extends from the pump 18 through the compartment 52 of the cover 16 internally past the tube 29 to exit the right side 34 of the cover 16 through a slotway 76 and then to the USB port 122 on the smart phone port 12. The phone male connector 72 is carried by a flat rectangular plate 78 which carries a number of connector posts 80. The posts 80 are sized to extend from an inner surface of the plate 78 into the slotway 76 in the right side 34 of the cover 16 to removably secure the plate 78 to the cover 16 when the male connector 72 is engaged within the USB port 122 on the smart phone 12. The slotway 76 through the sidewall 34 is preferably sized to permit the pump connector 70 to pass therethrough yet with the plate 78 closing the slotway 76 when the plate 78 is secured to the right side 34 of the cover 16.

The pump 18 is secured within the compartment 52 of the cover 16 with the pump outlet tube 56 extending through the left side 33 of the cover 16. While not shown, a manually operated discharge outlet plug may optionally be provided for manual manipulation between open and closed positions to open and sealably close the outlet tube 56.

The patch cord 20 electrically connects the pump 18 to the smart phone 12 and in so doing provides electrical power to the pump 18 with the smart phone 12 controlling when power is provided to the pump 18. Operation of the pump 18 will dispense fluid from the reservoir 14 out the discharge tube 56 preferably as a jet of liquid as schematically shown by the arrow A in FIG. 1. Various features of the smart phone 12 may activate the pump 18. The smart phone 12 preferably has a computerized control application stored in it providing for functionality as may be desired.

The dispenser assembly 10 may be placed on a flat surface as a tabletop and may be used to dispense the fluid from the discharge tube 56 as onto a user's hand. Alternatively, a dispenser assembly 10 may be held in one of a person's hands and activated to dispense fluid, for example, onto the other of a person's hand or an object.

Preferably, the fluid 46 within the reservoir 14 is a relatively low viscosity disinfecting or cleaning fluid such as alcohol or an alcohol and water based fluid.

In one preferred manner of operation, the smart phone 12 may be activated as by activating the smart phone 12 to receive voice commands after a user pushes the convenience key 124. Thereafter, with the smart phone 12 suitably programmed, on a user stating a word such as "dispense", the smart phone 12 would activate the pump 18 so as to dispense an individual dosage of the fluid. To dispense an individual dosage the pump is preferably operated for a set period of time. An individual dose of fluid may, for example, comprise 1 to 3 mm of the alcohol hand cleaner. Rather than merely use voice commands for activation of the pump 18, various other keys on the smart phone 12 could be used, for example, with the smart phone 12 to cause the pump 18 to dispense fluid on a user pushing the convenience key 116. As another example of operation the smart phone 12 could be programmed such that on a user holding down the convenience key 118, the pump would be operated continuously until the key 118 is released.

A preferred pump 18 in accordance with the present invention is a piezoelectric diaphragm micro pump as sold under the trade-mark CurieJet and having dimensions of approximately 25 mm by 24 mm by 10 mm and a pumping capacity of up to about 50 ml/min. Such pumps are described in U.S. Patent Publication US2011/0005606 published Jan. 13, 2011. Other pumps may be used without limitations.

In accordance with the present invention, the reservoir 14 may be refillable or alternately could be a single use reservoir to be replaced and discarded after the reservoir may be empty.

Figure 5:
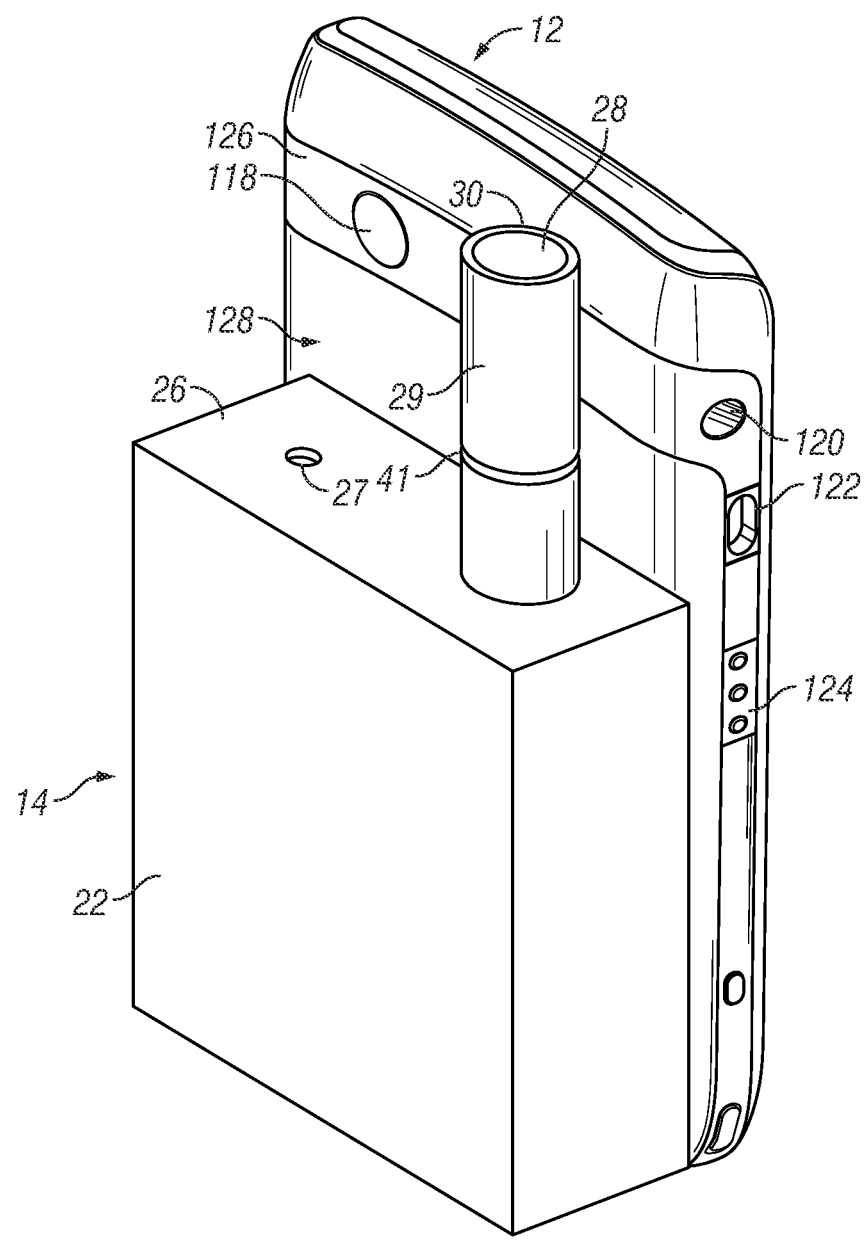
FIG. 5 is a rear pictorial view of the dispenser assembly as shown in FIG. 2, however, with a top cover and an associated pump mechanism removed.

The cover 16 preferably securely carries the pump 18 with the dip tube 57 and grommet 58 secured thereto to form a unit which can be in a snap fit manner coupled and removed from engagement with the reservoir 14. The reservoir 14, as best seen in FIG. 5, is physically secured to the battery cover 128 preferably with the reservoir 14 including the battery cover 122 integrally molded as one element.

Figure 10:
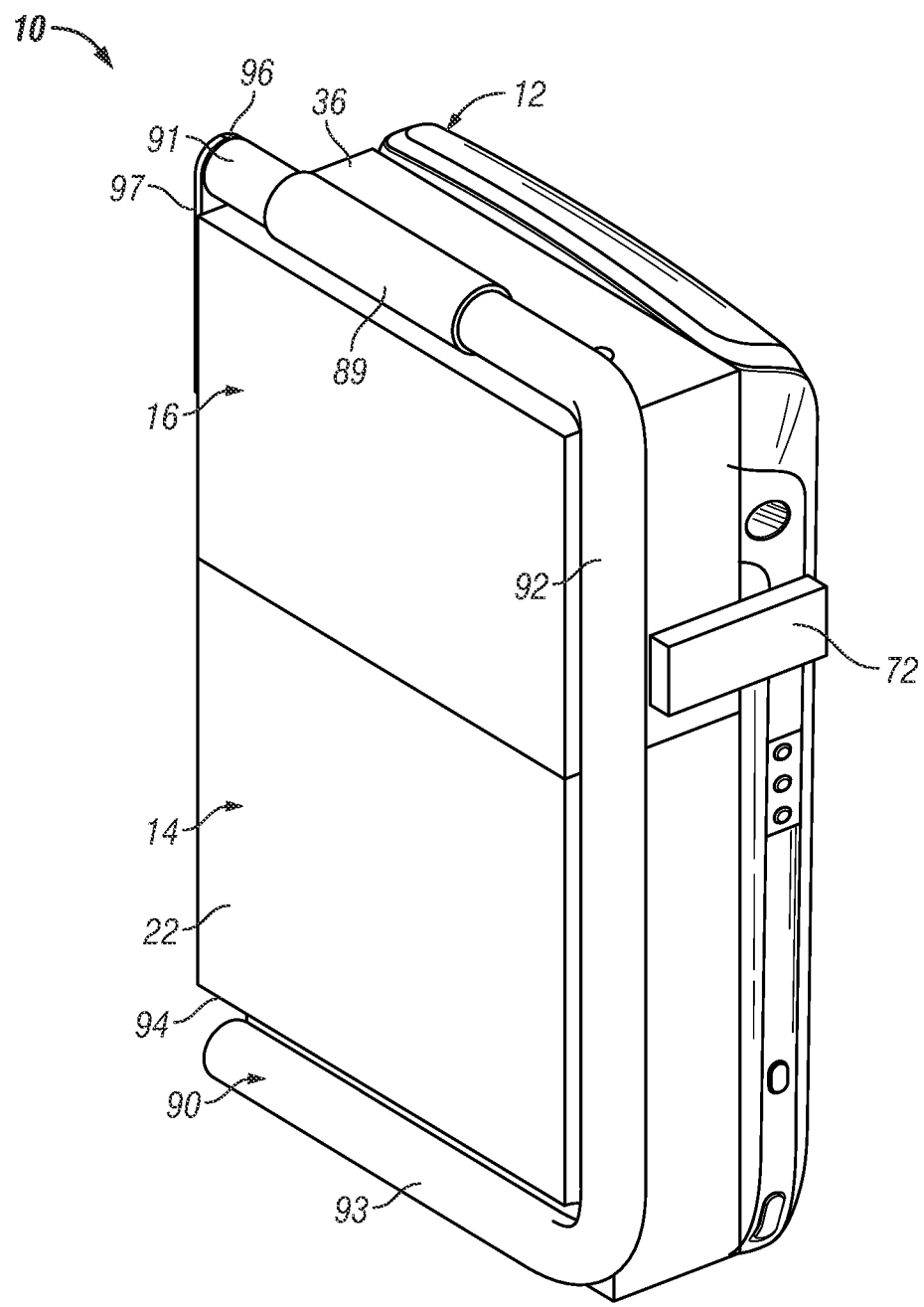
FIG. 10 is a rear pictorial view of a personal compliance dispenser assembly in accordance with a second embodiment of the present invention in a closed position.
Figure 11:
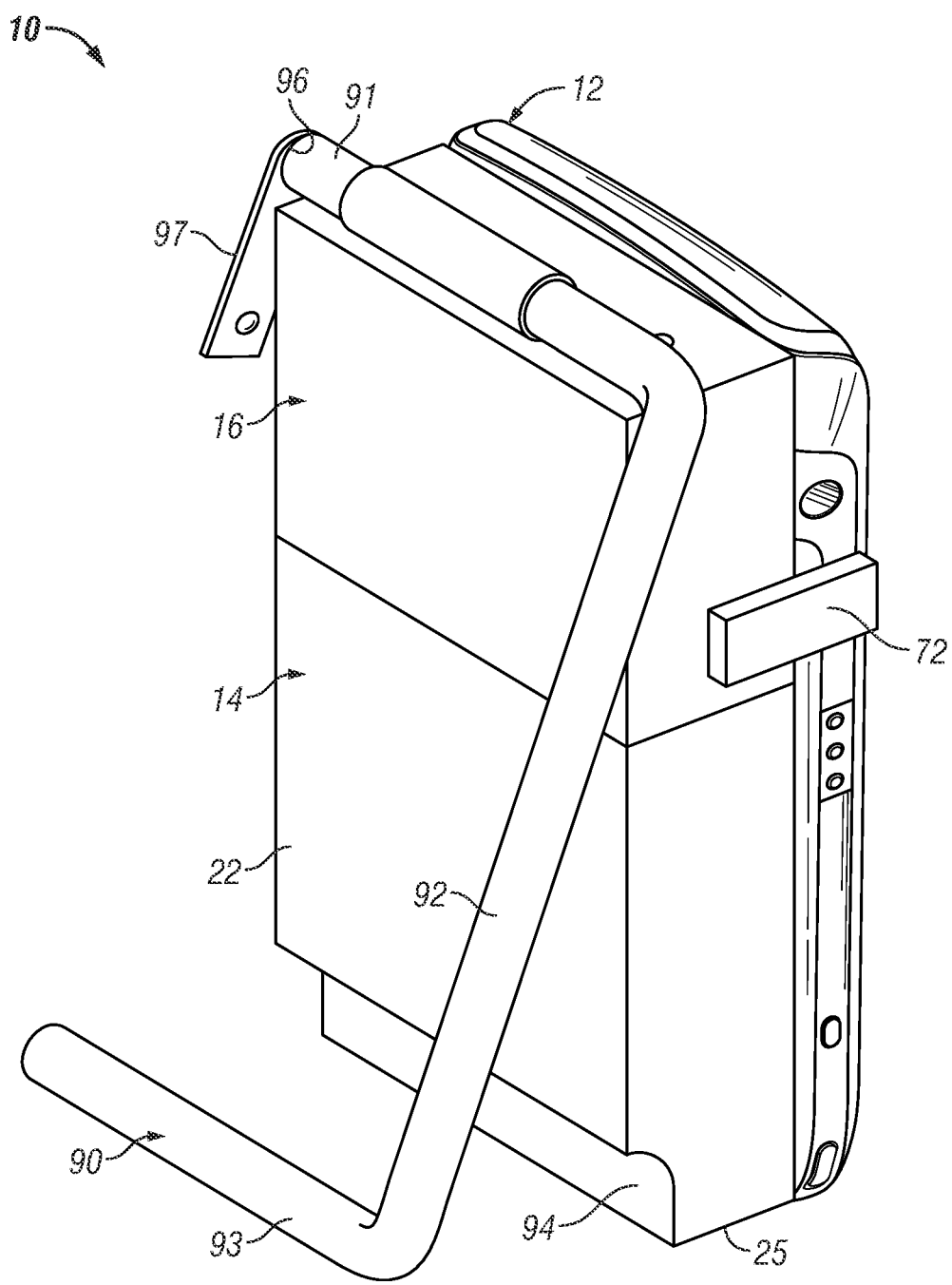
FIG. 11 is a rear pictorial view of the dispenser assembly shown in FIG. 10 in an open position.

Reference is made to FIGS. 10 and 11 which show a second embodiment of the dispenser assembly 10 in accordance with the present invention. The second embodiment is substantially the same as the embodiment illustrated in FIGS. 1 to 9, however, with the addition of a manually operated stand 90. The top 36 of the cover 16 is provided with a horizontal side to side tubular member 89 disposed above the air vent 48 and with the air vent 48 opening into the tubular member 89. The stand 90 is U-shaped and formed as from a cylindrical tube bent so as to have a first leg 91, a centre portion 92 and a second leg 93. The second leg 93 is parallel to the first leg 91. The first leg 91 extends through the tubular member 89 on the top 36 journalled therein so as to be rotated between a closed position shown in FIG. 10 and an open position shown in FIG. 11. The reservoir 14 is provided near its bottom 25 with a slot 94 cut into the back 22 above the bottom 25 which slot 94 is adapted to receive in a snap fit the second leg 92 so as to hold the stand 90 in a closed position as shown in FIG. 10. From the closed position, a user may engage the centre portion 92 of the stand 90 and pivot the stand 90 to the open position as shown in FIG. 11. The stand 90 can be useful in the open position in assisting the dispenser assembly 10 to sit on a surface against falling over.

The stand 90 may serve a support function merely to help support the dispenser assembly 10 as when placed on a flat surface. However the present inventor has appreciated that it is advantageous firstly to configure the dispenser assembly 10 to prevent leakage of fluid from the pump 18 outlet 56 and reservoir 14 when the dispenser assembly 10 is not in use as for example when the dispenser assembly 10 is in a wearer's pocket and secondly to configure the dispenser assembly 10 such that the pump 19 not be activated to dispense fluid except when desired, as for example to prevent accidental activation when the dispenser assembly 10 is in a wearer's pocket. The stand 90 in the preferred second embodiment is illustrated as but one mechanism for assist in preventing leakage of fluid and in restricting undesired activation of the pump.

FIG. 12 shows a cross-sectional end view through the top 36 of the cover 16 with the stand 90 in an open position. FIG. 12 shows in cross section the tubular first arm 91 coaxially received within the tubular member 89 of the top 36 of the cover 16. The cross section is at a location where the vent 48 extends through the top 36 into the inside of the tubular member 89. An air opening 95 is provided radially through the cylindrical side wall of the tubular first arm 91 which is in alignment with the air vent 48 when the stand 90 is in an open position as seen in FIG. 13, and in this open position the vent 48 is open to atmosphere coaxially through the tubular member 89. However, on moving the stand 90 to the closed position, as shown in FIG. 12, the air vent 48 is no longer in alignment with the air opening 95 and rather the engagement of the tubular first arm 91 of the stand 90 with the inside of the tubular member 89 sealably closes the air vent 48 against fluid passage therethrough when the stand 90 is in a closed position.

A distal end 96 of the first leg 91 of the stand 90 has secured thereto a radially extending resilient sealing arm 97. In the closed position, the sealing arm 97 overlies the outlet tube 56 sealable closing the same, however, when the stand 90 is moved to the open position, the sealing arm 97 pivots out of engagement with the outlet tube 56 permitting dispensing of fluid from the outlet tube 56. The stand 90, when in the closed position, sealably closes both the air vent 48 and the outlet tube 56 and thus assists in assuring that the dispenser assembly 10 if placed, for example, in a user's pocket in any orientation will not leak fluid. FIG. 12 also shows an electrical switch arrangement 300 including a first electrical contact 301 on the inside of the tubular member 89 and a second electrical contact 302 also on the inside of the tubular member 89 but a circumferentially spaced from the first electrical contact 301. An electrically conductive bridge member 304 is carried on cylindrical side wall of the tubular first arm 91. When the stand 90 is in an open position as seen in FIG. 13 the bridge member 304 engages and is in electrical contact with both the first electrical contact 301 and the second electrical contact 302 to permit electrical current to pass there through. In the closed position shown in FIG. 12, the bridge member 304 is located circumferentially out of engagement with the first electrical contact 301 such that the first electrical contact 301 and the second electrical contact 302 are circumferentially spaced out of engagement preventing electrical current to pass therebetween. The electrical switch arrangement 300 is shown schematically to have insulated lead wires 305 and 306 from each of the first electrical contact 301 and the second electrical contact 302 connected to a plug 307 which may be connected to the other electrical components such as for example to the pump 18 or the patch cord 20 or the male phone connector 72 to provide an input which is used to prevent operation of the pump when the electrical switch arrangement 300 is open.

Figure 14:
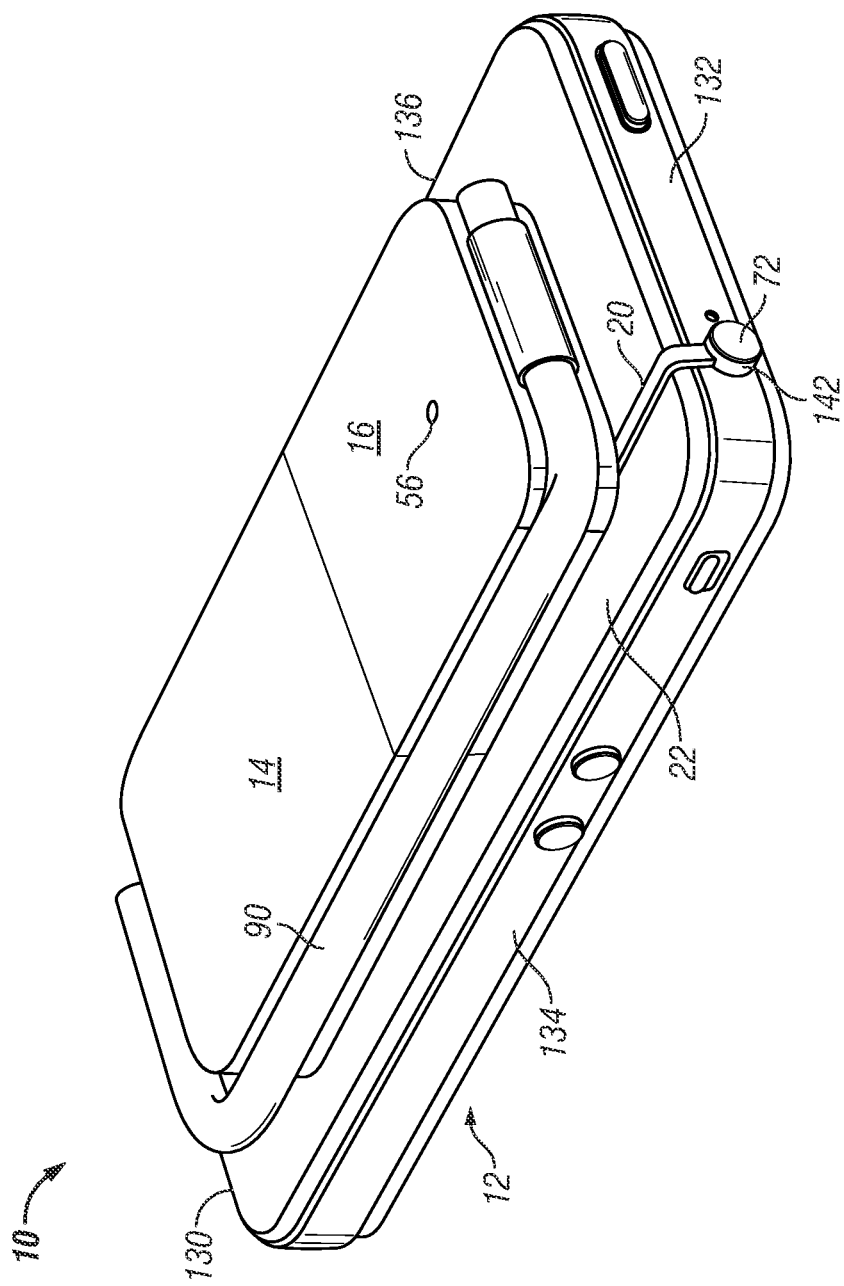
FIG. 14 is a rear pictorial view of a personal compliance dispenser assembly in accordance with a third embodiment of the present invention in a closed position.
Figure 15:
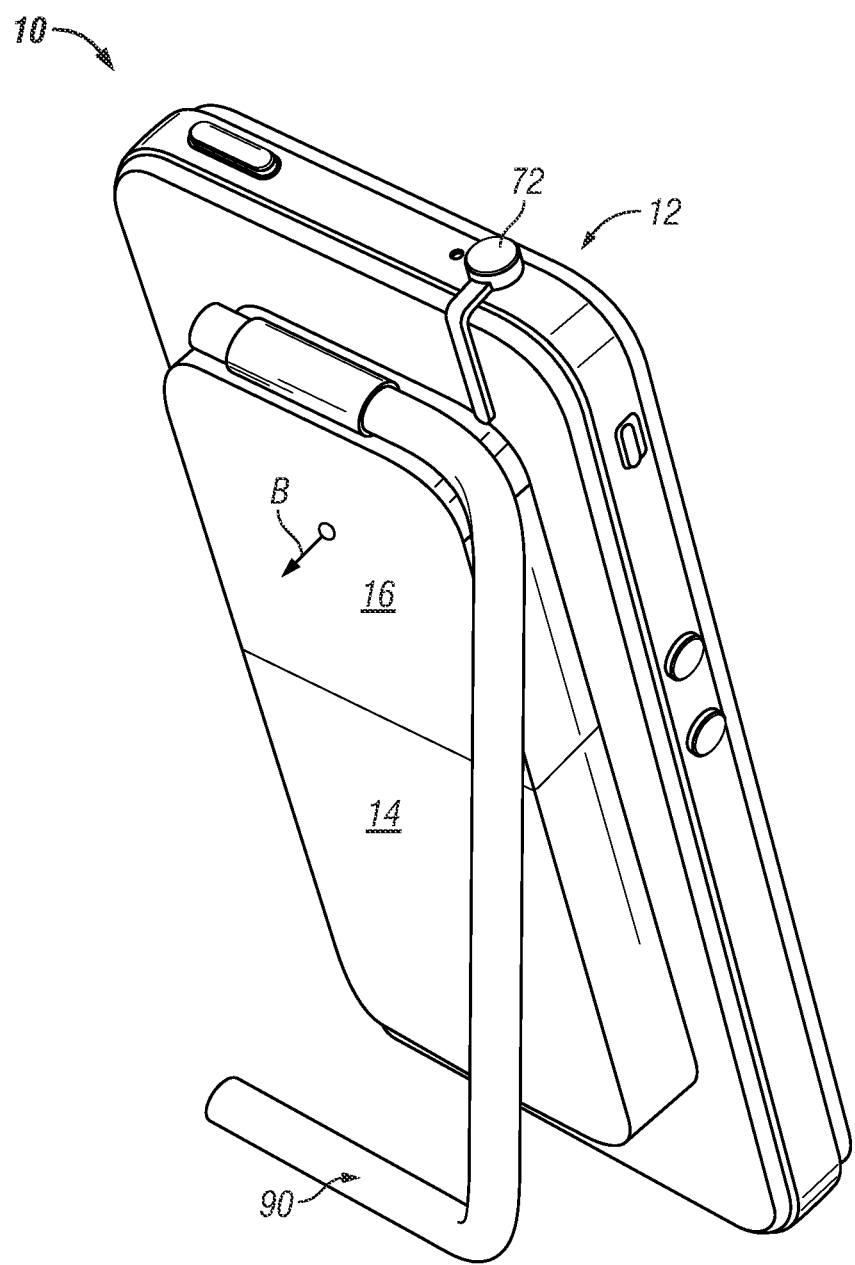
FIG. 15 is a rear pictorial view of the dispenser assembly shown in FIG. 14 in an open position.

Reference is made to FIGS. 14 and 15 which illustrate a third embodiment of a dispenser assembly 10 in accordance with the present invention. In this embodiment, the communication enabled, portable handheld pocket-sized, personal computer 12 is illustrated as a portable electronic multimedia communication device sold by Apple Inc. under the trade mark IPHONE, although a similar in appearance smart phone sold by Apple Inc. under the trade marks IPOD TOUCH could also be used and would appear the same. The IPOD TOUCH device may be considered a portable media player incorporating a personal digital assistant and a Wi-Fi platform. The smart phone 12 carries on its top 132 an audio jack 142. The reservoir 14, cover 16 and stand 90 are functionally the same as in the second embodiment of FIGS. 12 and 13. The reservoir 14 is bonded to the back 22 of the smart phone 12. A pump, not shown, is internally within the cover 16, however, has its discharge tube 56 extending outwardly from the back 32 of the cover 16 as adapted to dispense fluid onto a user's hand as in a stream of fluid schematically indicated by the arrows B in FIG. 15. In FIGS. 14 and 15, the reservoir 14, cover 16 and the stand 90 are sized to be smaller than the smart phone 12 and, as shown, do not extend beyond the top 132, bottom 130, side 134 or side 136 of the smart phone. A patch cord 20 is shown to make electrical connection between the audio jack 142 of the smart phone 12 and the pump within the cover 16. Insofar as the cell phone 12 may have a multi-pin port on its bottom 130, then a different patch card (not shown) could be used to electrically couple the multi-pin port to the pump 18.

Figure 16:
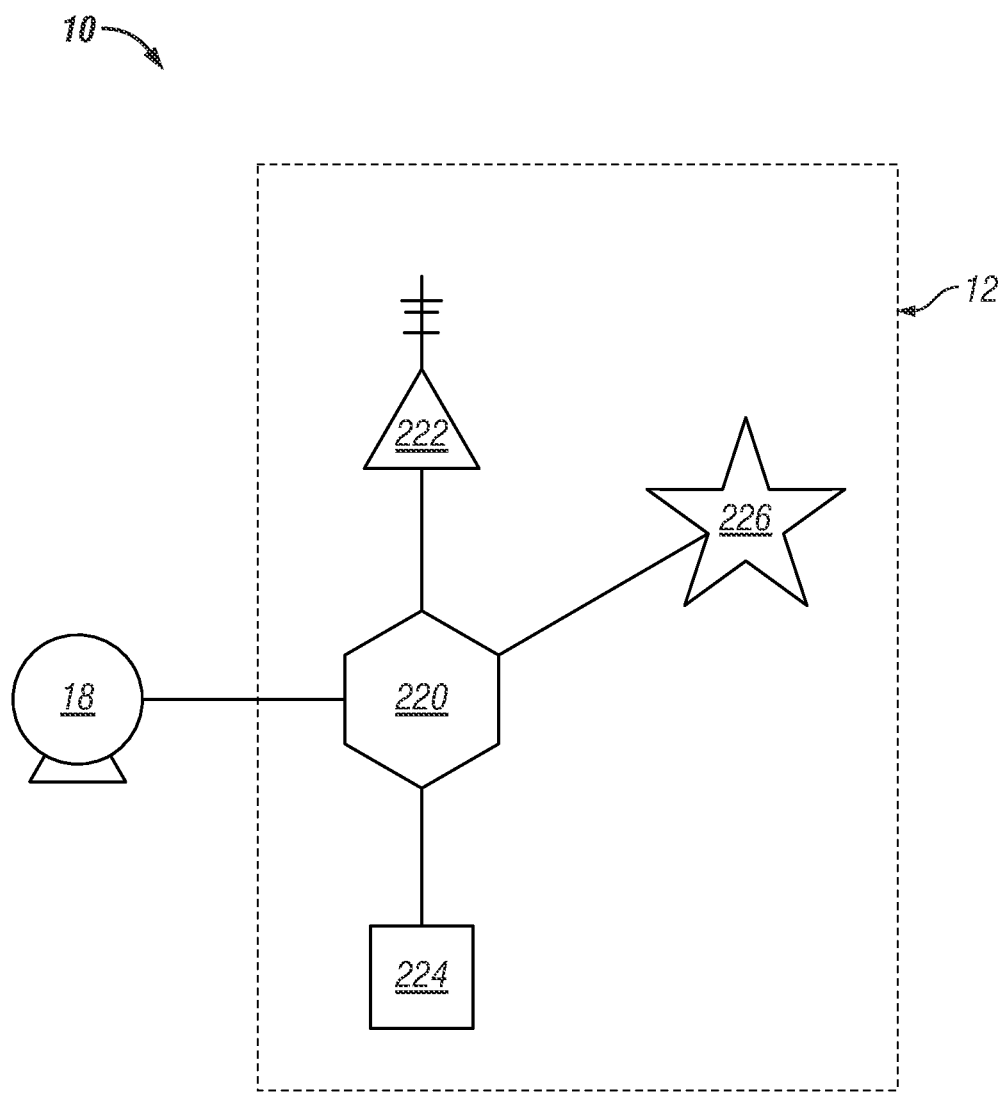
FIG. 16 is a schematic diagram showing the electrically powered components of a personal dispenser 10.

Reference is made to FIG. 16 which schematically illustrates a personal dispenser assembly 10 in accordance with any one of the first, second or third embodiments of the present invention. The smart phone 12 is schematically illustrated as including a computerized controller 220 which is electrically coupled to the pump 18. A battery 224 is shown to provide power to the controller 220 and the other components of the smart phone. A data communication module 222 is schematically shown and represents a system for one or two-way communication of data such as, for example, by well known methods including, for example, Wireless 3G communication as with a cell phone provider, Wi-Fi wireless communication and Bluetooth wireless communication, however, without limit. The various manners of input from a person carrying the cell phone 12 are schematically illustrated by input device 226 and may comprise, for example, manual input via keys, a touch screen and voice commands. It is well known that the controller 220 typically include a data storage system, an ability to store and operate various customized computerized applications, and various timing and clock functions. The data communication module 222 would also include various jacks for hardwiring communication of the controller 220 as to the pump and/or to other peripheral devices such as computer, network hubs and the like.

The pocket-sized personal computer 12 may optionally include a Global Positioning System (GPS) GPS capability such that the location of the personal hand hygiene compliance unit may be determined at any time and communicated as desired to a remote computer. GPS is a space-based global navigation satellite system (GNSS) that provides reliable location and time information. The location of the personal hand hygiene compliance unit can be useful so as, for example, to have the option to select monitoring information based on location, whether for example the location is within specific areas in a facility as in high infection risk areas or lower infection risk areas in the facility or whether the personal hand hygiene compliance unit is inside or proximate a facility or remote therefrom. Additionally, insofar as the personal hand hygiene compliance unit is desired to not leave a facility or an area in the facility then on receiving GPS data that the unit is being moved from a designated area a warning or alarm may be given as for example by an audible warning from the unit and/or a warning to security staff for the facility.

Rather than have GPS enablement the facility may have a location monitoring system with proximity sensors such as at specific locations or surrounding specific areas as with all access and exit locations for personnel being monitored by such proximity sensors being communication embowered sentry units which communicate with the personal hand hygiene compliance unit should any personal hand hygiene compliance unit be moved proximate thereto or through an access and exit location such that a central computer will be aware of the location or passage of the personal hand hygiene compliance unit as to monitor the same or to issue suitable notices, warnings or alarms based on the location information. As one example on a personal hand hygiene compliance unit being moved to outside of a facility or an area in a facility, an alarm could be sounded to assist in preventing the unit from being taken away from the facility. The alarm could be generated by the personal hand hygiene compliance unit, or at a location in the facility as at an exit doorway, or could be given to security personnel of the facility. In another example on a personal hand hygiene compliance unit entering an area of higher infection risk, a notice or warning could be given to the user of the increased risk, or a signal could be generated in or given to the personal hand hygiene compliance unit causing the unit to dispense an increased individual dosage of fluid towards increasing hygiene within an area of higher infection risk, or conversely a decreased dosage of fluid within an area of lower infection risk.

Figure 17:
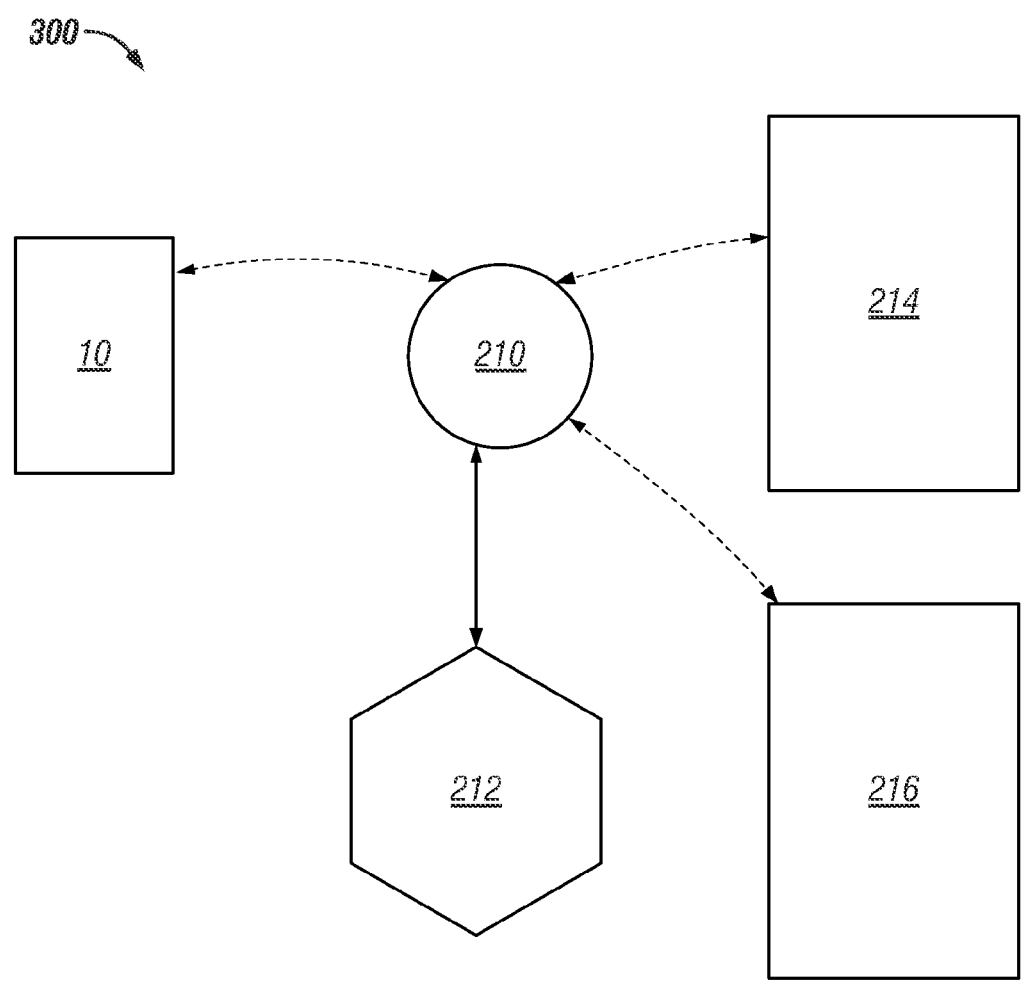
FIG. 17 is a schematic diagram showing a handwashing compliance system in accordance with the present invention including a personal compliance dispenser assembly in accordance with the present invention.

Reference is made to FIG. 17 which illustrates a hand washing compliance system 300 in accordance with the present invention and including as one element a personal dispenser assembly 10 in accordance with one of the embodiments of the present invention. The system is shown to include a wireless hub 210 serving to interconnect the dispenser assembly 10 with a computer 69. In addition to the personal dispensing assembly 10, the system is shown as containing a manually operated fluid dispenser 214 and a touch less electrically operated fluid dispenser 216. The manually operated fluid dispenser 214 may be of a type, for example, disclosed in U.S. Patent Publication 2010/0288788 to Ophardt, published Nov. 18, 2010 and which provides in the context of a manually operated dispenser, the ability to communicate preferably wirelessly with the wireless hub 210. The touchless electrically powered fluid dispenser 216 may comprise a touchless dispenser of the type disclosed in U.S. Patent Publication 2009/0045221, published Feb. 19, 2009 which may, for example, be powered by batteries and have a capability of communicating wirelessly or via wires with the wireless hub 210. The handwashing compliance system 300 shown in FIG. 17 may be adopted for use as, for example, in a hospital in which a plurality of such personal dispenser assemblies 10, a plurality of such manually operated dispensers 214 and a plurality of such touchless automated dispensers 216 may be used throughout the hospital facility. Each dispenser has a capability of transmitting data about the usage of the dispenser to a remote central computer 212 which data can be gathered in an appropriate manner to assist persons skilled in the art in determining whether handwashing criteria have been complied with. The particular nature of the data which is transferred, for example, from the personal dispenser assembly 10 is not limited but may include information as to the times that a dosage of fluid is dispensed and identification of the personal dispensing assembly. Such data may be received, stored and analyzed by the remote computer 212 for processing compliance.

The particular nature of the communication and transfer of data from the personal dispenser assembly 10 to the computer 212 and/or possibly from the computer 212 to the personal dispenser assembly 10 is not limited. The pocket-sized personal computer 12 of the personal dispenser assembly 10 may have the capability to instantly transmit data about dispensing whenever fluid is dispensed or, alternatively, to store such data and process the data as appropriate for delivery at desired or selected times as, for example, on periodic time intervals or to provide such data when it may receive a prompt command from a user or from a remote computer 212. The pocket-sized personal computer 12 may also keep track as to the volume of fluid remaining in the reservoir and may provide warnings and indications as to fluid levels in the reservoir 14 and when the reservoir 14 needs to be replaced or refilled. Such data regarding the level of fluid in the reservoir 14 may be maintained and calculated within the pocket-sized personal computer 12 or, alternatively, may be maintained and calculated by the central remote computer 212 and communicated to the smart phone. Various systems, methods and warnings may be used to provide warning and instructions to a user of the cell phone regarding fluid levels in the reservoir, prompts to use the dispenser assembly 10 to clean the user's hands and warnings regarding non-use.

The first, second and third embodiments illustrated in FIGS. 1 to 15 illustrate arrangements in which the pump 18 is an electrical pump powered by the battery 224 of the pocket-sized personal computer 12. This is not necessary. The pump 18 in the dispenser 13 may comprise an electrically operated pump which is powered by a battery carried by the dispenser 13, for example, within the cover 16 or in a sealed compartment within the reservoir 14. Where the fluid to be dispensed by the reservoir is alcohol, as a source of power may comprise a fuel cell which uses the fluid to generate power.

Figure 18:
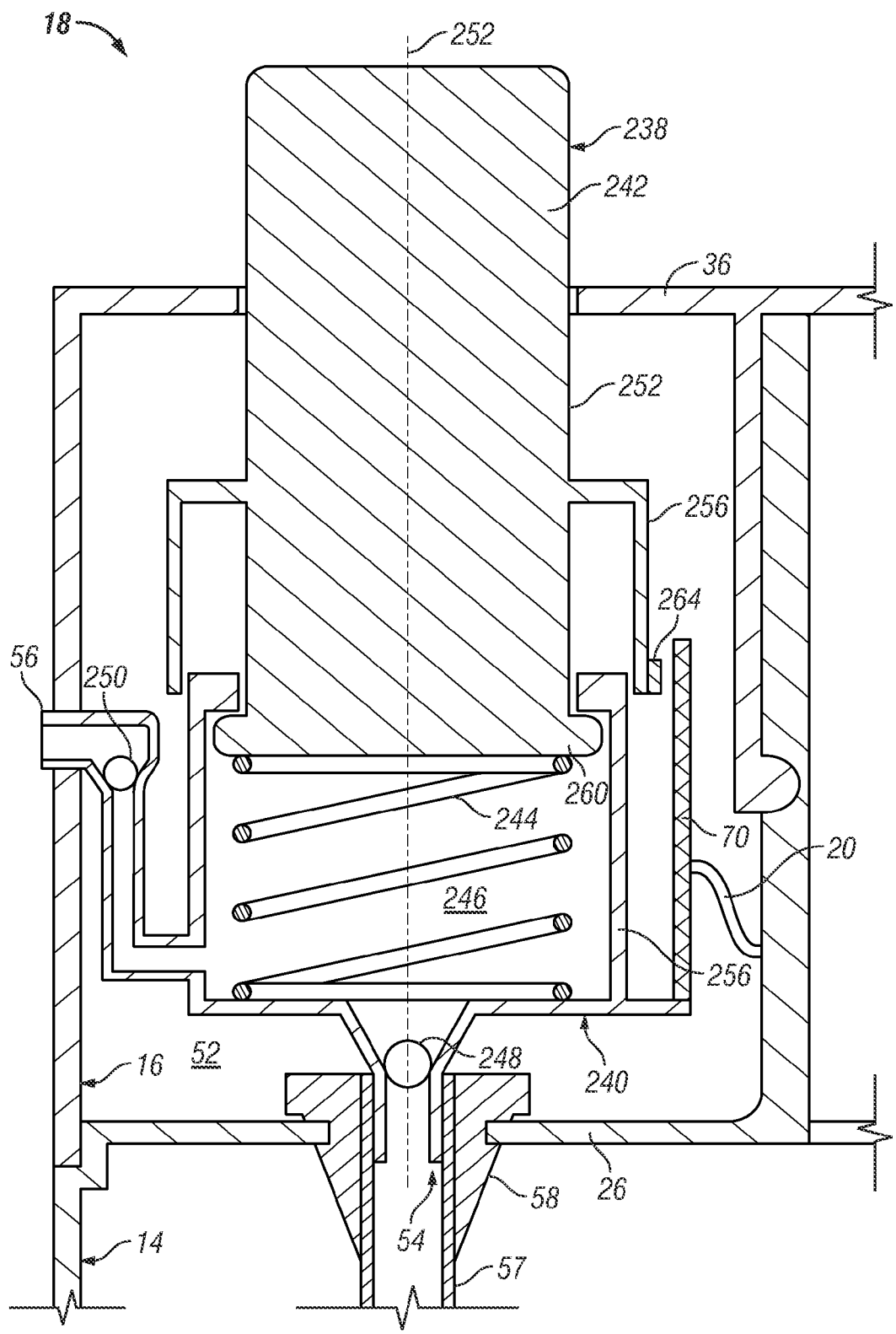
FIG. 18 is a vertical cross-sectional rear view similar to that shown in FIG. 6 but of a personal compliance dispenser assembly in accordance with a fourth embodiment to the present invention.

The pump 18, however, need not be electrically powered and may be a manually operated pump and, in this regard, reference is made to FIG. 18 which shows a vertical cross-sectional rear view similar to FIG. 6 but showing a personal dispenser assembly 10 in accordance with a fourth embodiment of the present invention. The dispenser assembly 10 shown in FIG. 18 is the same as that shown in FIG. 6 with the exception that a manually operated pump 18 is provided and the patch cord 20 is modified to replace the male pump connector 70 with a pick up device also indicated as 70 in FIG. 18.

The manually operated pump is schematically illustrated as comprising a piston pump 238 having a piston chamber-forming body 240 within which a piston 242 is axially slidable and biased to an outer position as by a spring 244. The piston extends outwardly beyond the top 36 of the cover 16 for engagement by the user. On a user depressing the piston 242 against the bias of the spring 244, fluid is dispensed out the fluid outlet tube 56. Between the dip tube 57 and a fluid chamber 246 formed within the pump, there is an inlet one-way valve 248 which permits flow outwardly from the reservoir 14 through the inlet tube 54 into the chamber in the pump. As well, there is a one-way outlet valve 250 providing output from the chamber 246 to the outlet tube 56 merely outwardly from the chamber. The piston 242 has a piston head 260 which is sealably engaged within the piston chamber-forming body 240 and each is cylindrical and coaxial about a central axis 252. The piston 242 is shown as carrying a cylindrical inner wall 254 and a cylindrical outer wall 256. The body 240 has a cylindrical wall 258 with a catch shoulder to engage on a catch shoulder on the piston head 260 to stop the piston from being slid axially fully out of the piston chamber-forming body. After the piston 242 has been depressed by a user, on release the spring 244 urges the piston outwardly and draws fluid from the reservoir 14 into the chamber 246.

In FIG. 18, the pick up device 70 is shown as carried on an end of the patch cord. The other end of the patch cord is in engagement in a port of the smart phone 12. The purpose of the pick up device 70 is to provide a signal to the smart phone 12 as to when the piston 248 has been moved in each stroke of operation. The pick up device 70 includes a magnetic sensor which senses when the magnet on the piston has moved past a sensor on the pick up device 70 and convert this to an electrical signal transferred to the smart phone.

Figure 19:
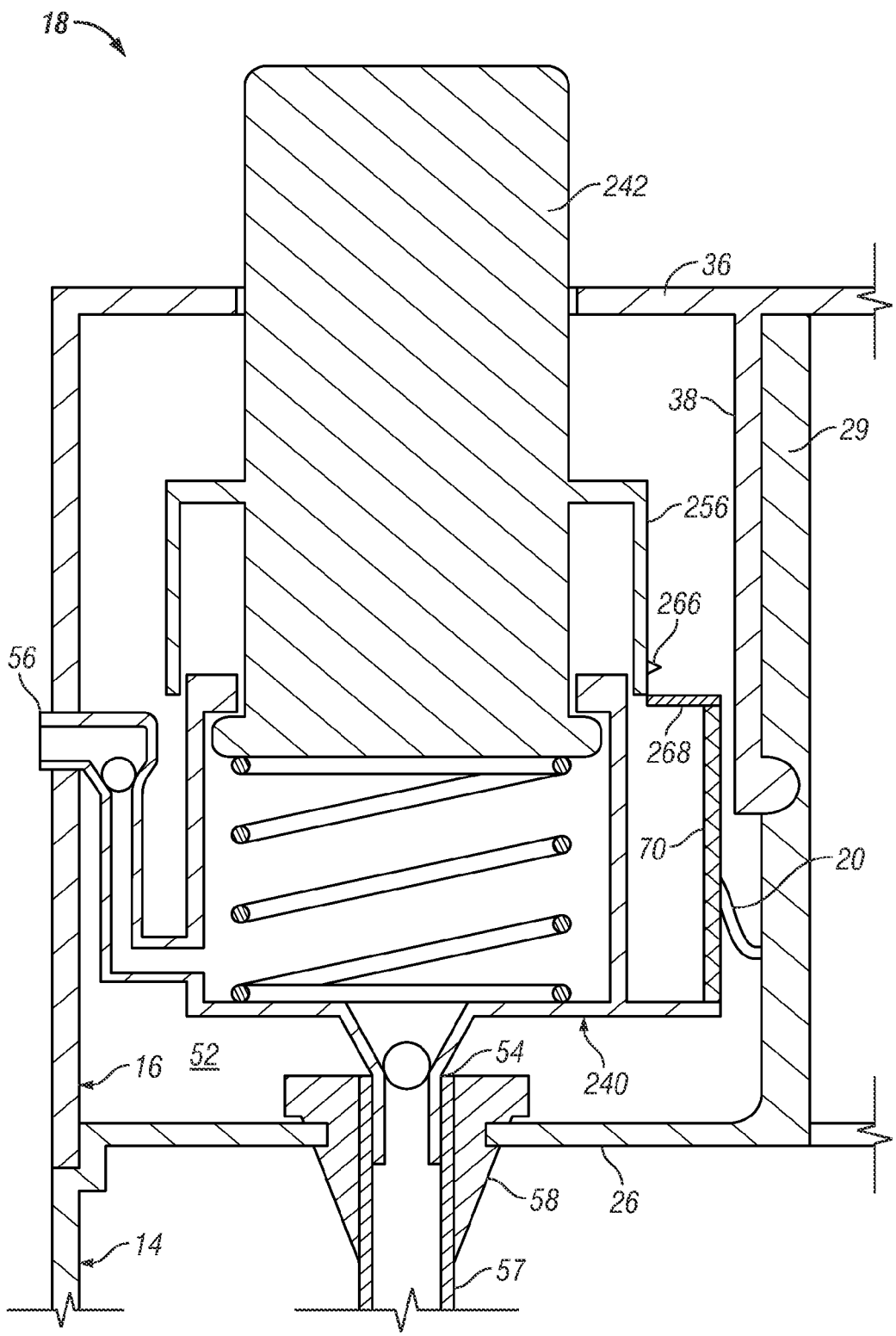
FIG. 19 is a vertical cross-sectional rear view similar to that shown in FIG. 6 but of a personal compliance dispenser assembly in accordance with a fifth embodiment to the present invention.

FIG. 19 illustrates a fifth embodiment of a dispenser assembly 10 which is identical to the fourth embodiment but with the magnet 264 replaced by a shoulder 266 carried on the outer wall 256 of the piston and adapted to engage a sound producing deflectable reed 268 carried on the pick up device 70. On the piston moving in a stroke of operation, the shoulder 266 engages the reed 268 such that the reed 268 is deflected to produce a sound. The sound is deflected by the pick up device 70 and a signal transferred to the smart phone. In the embodiment of FIG. 19, the sound could either be picked up by the pick up device 70 or, alternately, the pick up device could be removed and the sound could be picked up directly by a microphone carried on the smart phone 12 without the need for the patch cord.

Figure 20:
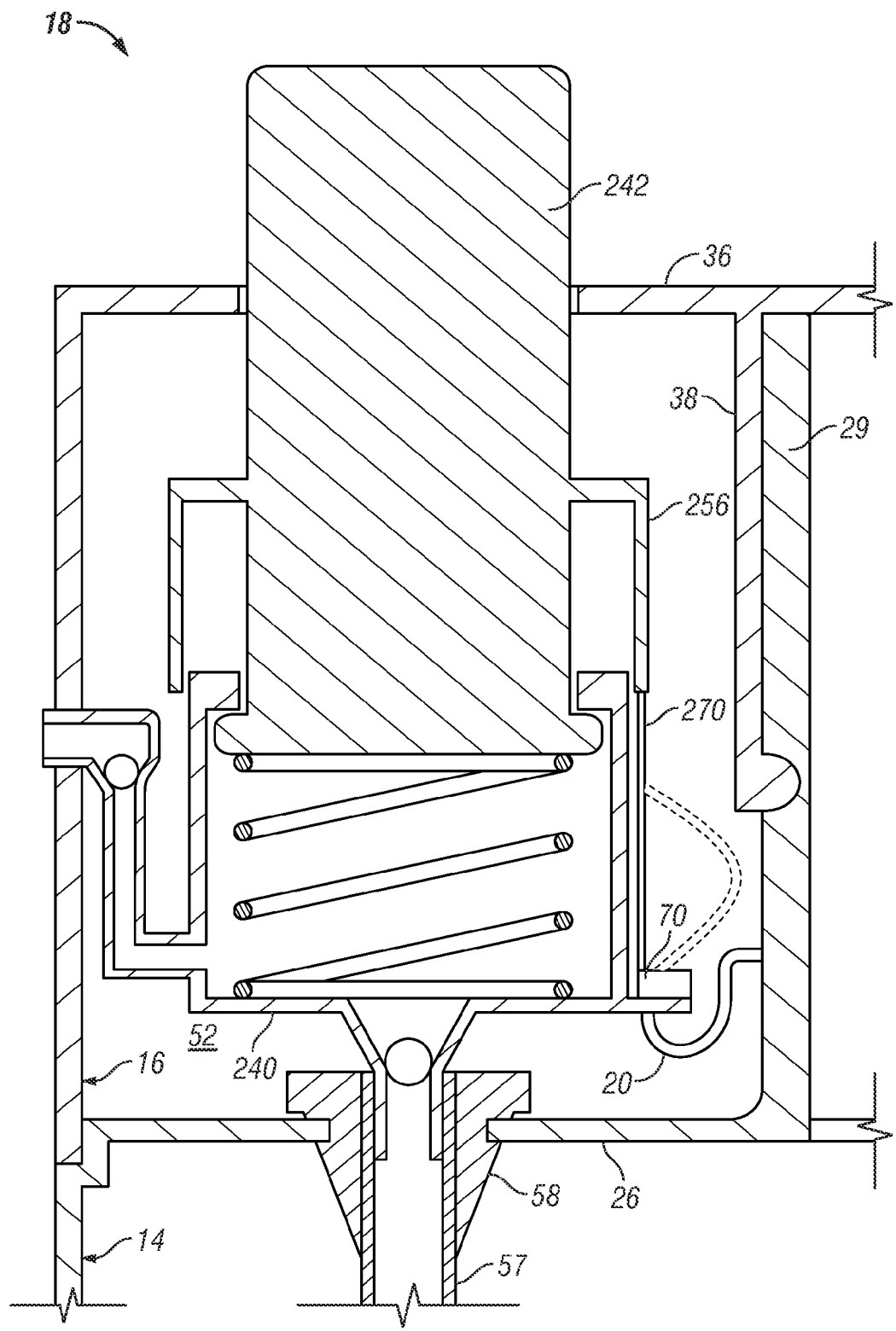
FIG. 20 is a vertical cross-sectional rear view similar to that shown in FIG. 6 but of a personal compliance dispenser assembly in accordance with a sixth embodiment to the present invention.

FIG. 20 illustrates a sixth embodiment of a dispenser assembly 10 which is identical to the fourth embodiment but with the magnet 264 replaced by a piezoelectric generator 270 coupled between the piston 242 and the body 240 for deflection with movement of the piston from a position shown in solid lines in FIG. 20 to a deflected position shown in dashed lines. With such deflection, the generator 270 generates electrical power which is transmitted to the smart phone.

In the second embodiment of FIGS. 10 to 13 with an electrically powered pump, the stand 90 when moved to the closed position opens the electrical switching mechanism 300 to prevent operation of the pump. In the embodiments of FIGS. 18. 19 and 20 with manually operated pumps, a block member may be provided for manual movement between a blocking position in which the block member prevents movement of the piston 242 and an unblocked position in which movement of the piston 242 is not prevented. The block member can be coupled to a stand such as stand 90 in the second embodiment such that movement of the stand 90 to the open position moves the block member to the unblocked position and movement of the stand 90 to the closed position moves the block member to the blocked position.

The particular nature of the pump to be used as a manual pump is not limited and it may comprise various forms of bellows, piston, peristaltic and other type pumps as are well known to persons skilled in the art.

The invention has been described with reference to preferred embodiments. For a definition of the invention, reference is made to the following claims.

I claim:

1. A personal hand hygiene monitoring unit carried on a person for monitoring of hand hygiene,
   the unit comprising a hand sanitizing fluid dispenser and a portable handheld pocket-sized personal computing device,
   the dispenser comprising a dispenser housing, a reservoir for containing a fluid, a pump and a discharge outlet,
   the dispenser housing carrying the reservoir, the pump and the discharge outlet,
   the pump coupled to the reservoir,
   the pump is a manually operated pump in which a piston is moved by a user to dispense the fluid from the reservoir out the discharge outlet,
   the dispenser including a sound producing reed which generates a sound when the piston is moved by a user to dispense the fluid,
   wherein on the piston being moved by a user to dispense the fluid, the piston engages the reed and the reed is deflected by the piston to produce the sound,
   the computing device having a computer housing, and within the computer housing a controller, a user interface, a battery, a microphone for sensing the sound, and a data communication device for transmission of data from the computing device,
   the dispenser housing mechanically coupled to the computer housing,
   the controller monitoring when the pump is activated by sensing the sound with the microphone and providing for the transmission via the data communication device the data representative of the sound sensed by the microphone to a remote computer.

2. A unit as claimed in claim 1 wherein the computing device has a removable battery cover covering a substantial portion of surface of the computing device, the dispenser fixedly secured against removal to the battery cover.

3. A unit as claimed in claim 1 including a stand coupled to the unit and movable between a closed position in which the stand lies proximate to the unit and an open position in which the stand extends away from the unit for engaging a horizontal support surface to support the unit on the support surface with the discharge outlet at a location relative the surface that fluid may be discharged from the dispenser onto a person's hand adjacent the outlet and above the surface.

4. A unit as claimed in claim 3 wherein the stand is pivotally mounted to the dispenser for pivoting between the closed position and the open position.

5. A unit as claimed in claim 1 wherein the data communication device is communication enabled for Wi-Fi communication capability.

6. A unit as claimed in claim 1 wherein the computing device is selected from the group consisting of a cell phone, smart phone and a personal digital assistant.

7. The unit as claimed in claim 1 in which the pump is a piston pump in which the piston is reciprocally movable relative to a piston chamber-forming body.

8. The unit as claimed in claim 7 in which the piston chamber-forming body is fixedly secured to the dispenser housing,
   reed is carried on the dispenser housing.

9. A unit as claimed in claim 7 including a stand coupled to the unit and movable between a closed position in which the stand lies proximate to the unit and an open position in which the stand extends away from the unit for engaging a horizontal support surface to support the unit on the support surface with the discharge outlet at a location relative the surface that fluid may be discharged from the dispenser onto a person's hand adjacent the outlet and above the surface.

10. A unit as claimed in claim 7, wherein the computing device is selected from the group consisting of a cell phone, smart phone and a personal digital assistant.

11. A personal hand hygiene unit carried on a person for monitoring of hand hygiene, the unit comprising a hand sanitizing fluid dispenser and a portable handheld pocket-sized personal computing device, the dispenser comprising a dispenser housing, a reservoir for containing a fluid, a pump and a discharge outlet, the dispenser housing carrying the reservoir, the pump and the discharge outlet, the pump coupled to the reservoir, the pump is a manually operated pump in which a piston is moved by a user to dispense the fluid from the reservoir out the discharge outlet, the dispenser including a sound producing reed which generates a sound when the piston is moved by a user to dispense the fluid, wherein on the piston being moved by a user to dispense the fluid, the piston engages the reed and the reed is deflected by the piston to produce the sound, the computing device having a computer housing, and within the computer housing a controller, a user interface, a battery, a microphone for sensing the sound, and a data communication device for transmission of data from the computing device, the dispenser housing mechanically coupled to the computer housing, the controller monitoring when the pump is activated by sensing the sound with the microphone and providing for the transmission via the data communication device the data representative of the sound sensed by the microphone to a remote computer, the unit including a stand coupled to the unit and movable between a closed position in which the stand lies proximate to the unit and an open position in which the stand extends away from the unit for engaging a horizontal support surface to support the unit on the support surface with the discharge outlet at a location relative the surface that fluid may be discharged from the dispenser onto a person's hand adjacent the outlet and above the surface.

12. A unit as claimed in claim 11 wherein the stand is pivotally mounted to the dispenser for pivoting between the closed position and the open position.

13. A unit as claimed claim 12 wherein the computing device is selected from the group consisting of a cell phone, smart phone and a personal digital assistant.

* * * * *